United States Patent [19]

Kitzelmann et al.

[11] 4,394,239
[45] Jul. 19, 1983

[54] ELECTRO-CHEMICAL SENSOR FOR THE DETECTION OF REDUCING GASES, IN PARTICULAR CARBON MONOXIDE, HYDRAZINE AND HYDROGEN IN AIR

[75] Inventors: Dieter Kitzelmann, Bonn; Jacques Deprez, Frechen, both of Fed. Rep. of Germany

[73] Assignee: Bayer Aktiengesellschaft, Leverkusen, Fed. Rep. of Germany

[21] Appl. No.: 295,277

[22] Filed: Aug. 24, 1981

[30] Foreign Application Priority Data

Sep. 9, 1980 [DE] Fed. Rep. of Germany ....... 3033796

[51] Int. Cl.³ ............................................ G01N 27/54
[52] U.S. Cl. ..................................... 204/414; 204/1 T
[58] Field of Search ........... 204/1 T, 1 N, 1 K, 195 R

[56] References Cited

U.S. PATENT DOCUMENTS

| | | | |
|---|---|---|---|
| 4,049,503 | 9/1977 | Becker et al. | 204/1 T |
| 4,141,800 | 2/1979 | Breuer et al. | 204/1 T |
| 4,149,948 | 4/1979 | Petersen et al. | 204/195 R |
| 4,207,162 | 6/1980 | Lotze | 204/195 R |
| 4,227,974 | 10/1980 | Petersen et al. | 204/1 T |
| 4,227,984 | 10/1980 | Dempsey et al. | 204/195 S |

FOREIGN PATENT DOCUMENTS

2155935  6/1972  Fed. Rep. of Germany ... 204/195 R
2316365 10/1974  Fed. Rep. of Germany ... 204/195 R

OTHER PUBLICATIONS

H. W. Bay et al., International Laboratory, pp. 37–41, Sep./Oct. 1972.

*Primary Examiner*—G. L. Kaplan
*Attorney, Agent, or Firm*—Sprung, Horn, Kramer & Woods

[57] ABSTRACT

A sensor consists of a catalytically active measuring electrode communicating with a non-polarizable atmospheric oxygen electrode by way of an aqueous acid electrolyte. The electrolyte used is an aqueous gelatinous polymeric adhesive in which ionogenic substances are dissolved. Due to the adhesive properties of the electrolyte, a 3-phase boundary of air-catalyst-electrolyte is formed at the transition to the measuring electrode and substantially determines the measuring process.

4 Claims, 1 Drawing Figure

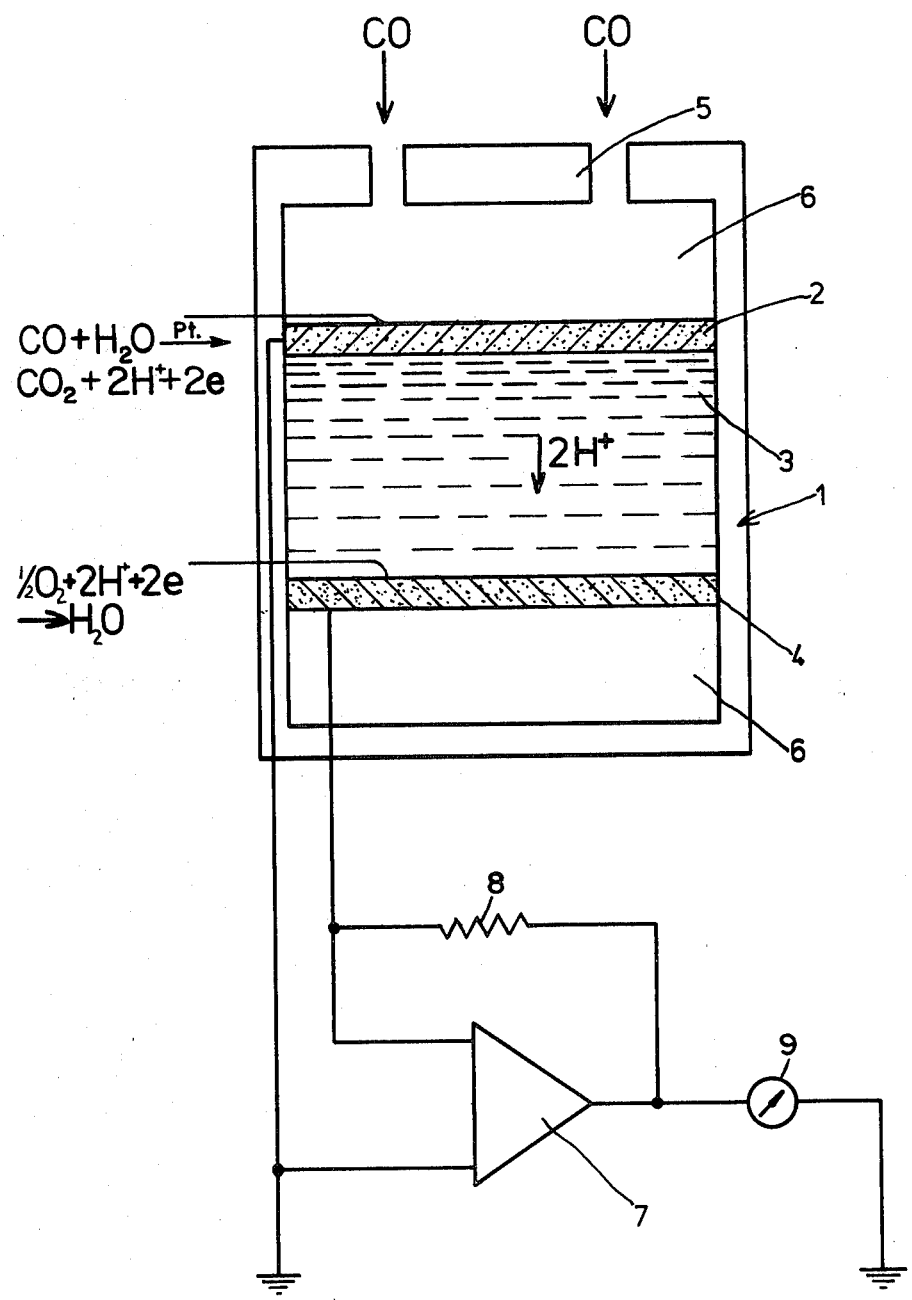

ELECTRO-CHEMICAL SENSOR FOR THE DETECTION OF REDUCING GASES, IN PARTICULAR CARBON MONOXIDE, HYDRAZINE AND HYDROGEN IN AIR

BACKGROUND OF THE INVENTION

This invention relates to an electro-chemical sensor for measuring carbon monoxide, hydrogen or hydrazine in the surrounding atmosphere, comprising a polarizable, catalytically active measuring electrode which is exposed to the surrounding air and communicates by way of an aqueous acid electrolyte with a non-polarizable atmospheric oxygen electrode as counter electrode.

In immission monitoring, and to some extent also in emission monitoring, it is necessary nowadays to detect traces of gas at extremely low concentrations. This requires measuring processes of the utmost sensitivity. For example, limiting exposure to carbon monoxide is one of the most extensive and urgent problems in many fields or industry. Environmental pollution by carbon monoxide is caused by incomplete combustion, e.g. of engine fuels or domestic fuels. Due to the toxicity and risk of explosion, combined with the impossibility of recongnizing the pollutant by color, odor or taste, monitoring of the concentrations is necessary and this should be as far as possible continuous.

It was therefore an object of the present invention to develop a gas detector to measure the concentrations of harmful substances. The device should be suitable for use by technically unskilled operators and therefore relatively easy to handle, should function according to a simple, reliable method of measuring and should be ready for taking measurements as soon as it is switched on.

Apart from purely chemical and physical measuring methods, electro-chemical methods are frequently used for the determination of carbon monoxide, hydrogen and hydrazine. Measuring cells with 3-electrode arrangements have been proposed for the measurement of carbon monoxide (see. H. W. Bay, K. F. Blurton, H. C. Lieb, H. G. Oswin, International Laboratory, vol. 1, 1972, No. 5, pages 37 to 41; U.S. Pat. Nos. 3,824,167 (1974) 4,013,522 (1977); German Offenlegungsschrift No. 2,155,935 (1972). These are analogous to the usual half cell arrangements used in electro-chemistry, in which carbon monoxide is oxidized in aqueous solutions at noble metal electrodes, mainly platinum, at potentials of +0.9 to 1.5 V against a standard hydrogen electrode, in accordance with the following equation:

$$CO + H_2 \rightarrow CO_2 + 2H^+ + 2C$$

The measuring cell consists of measuring electrode, a counter electrode and a reference electrode. The potential of the measuring electrode with respect to the reference electrode is adjusted by means of an electronic potentiostat (voltage source) and maintained constant within the required range. The carbon monoxide diffusing towards the measuring electrode is oxidized at that electrode and an electric current proportional to the carbon monoxide concentration is produced.

Alternative proposals include measuring cells consisting of 2-electrode arrangements where carbon monoxide is oxidized at the anode and the counter electrode (cathode) either contains an active substance (oxides or mixed oxides of transition elements) whose redox potential polarizes the anode to the desired electrode potential of +0.9 to 1.5 V (see German Offenlegungsschrift No. 23 16 365) or consists of a gas electrode at which atmospheric oxygen, for example, is reduced. The dimensions of the cathode are selected so that the potential of the cathode does not vary with the measuring currents produced.

Arrangements comprising a reference electrode or a counter electrode functioning as a reference point do not operate completely satisfactorily because the reference potential varies over a period of time. This means that the potential of the measuring electrode also changes so that the primary current is liable to increase in the positive or negative direction due to the reduction at atmospheric oxygen or the formation of oxide layers on the surface of the measuring electrode. Since it is virtually impossible to achieve a constant potential when a reference electrode is used, this measuring system is more susceptible to trouble.

In sensors which are used in portable gas warning instruments or in small telemetering equipment, as in the described invention, it is advisable to replace the liquid electrolytes by solid electrolytes or to fix the electrolytes in order to avoid outflow of the acid frequently used as electrolyte. One known method is immobilization simply by suction, e.g. in asbestos powder, quartz powder or a porous organic or inorganic matrix, e.g. porous PVC filter discs or porous glass filter paper. Fine grained ionic exchange resins which absorb aqueous electrolytes may also be used to fix the electrolyte. When such sensor cells are in operation, the volume of the electrolyte is reduced due to loss of water by evaporation, with the result that the contact between electrode and electrolyte can no longer be maintained and the sensitivity of measurement is therefore reduced.

SUMMARY OF THE INVENTION

It is an object of the present invention to develop electro-chemical sensors for the measurements of carbon-monoxide, hydrazine or hydrogen in air on the basis of immobilized electrolytes with rapid response and a very low primary current.

To solve this problem in accordance with the invention, the electrolyte consists of an aqueous, gelatinuous polymeric adhesive in which ionogenic substances are dissolved, and the measuring electrode is a current-abducting matrix containing the catalyst, the adhesive properties of the electrolyte together with the electrode resulting in a 3-phase boundary of ambient air- catalyst-electrolyte.

The acid aqueous phase of the electrolyte is a homogeneous system, i.e. the aqueous acid constituents are incorporated by polymerization when cross-linking takes place. The current producing electrochemical reaction takes place on those catalyst particles which have part of their surface embedded in the electrolyte but are otheriwse exposed to ambient air and are in addition in electrical contact with the matrix. The essential criteria for the measuring effect is thus the above mentioned 3-phase boundary.

By "matrix" is meant here a porous sheet-like structure, e.g. a fleece or grid of electrically conductive materials.

The good adhesive properties of the electrolyte surface ensures good mechanical adherence of the two electrodes. The intimate contact between electrodes and electrolyte ensures optimal development of the 3-phase boundary which is so important for the electrochemical reaction. In conventional gas diffusion electrodes having a 3-phase zone of electrode-electrolyte-gas, the gas must either be delivered to the electrode under pressure or the electrode must be rendered hydrophobic in order to prevent over filling of the electrodes system of pores with electrolyte and spilling of the electrolyte, (see W. Vielstich, Brennstoffelemente, pages 4 and 5, publishers Chemie, Weinheim 1965).

BRIEF DESCRIPTION OF THE DRAWING

The basic construction of the measuring cell is shown in the FIGURE and is described below with reference by way of example to a CO-cell.

DETAILED DESCRIPTION OF THE INVENTION

A cylindrical body 1 of plastic, e.g. polypropylene, contains an aqueous gel electrolyte 3. A measuring electrode 2 and counter electrode 4 are not constructed as gas diffusion electrodes as in fuel cells, but are firmly bonded to the gel electrolyte due to the adhesive properties of the latter. Both the measuring electrode and the counter electrode may be differently constructed according to the given measuring problem and may contain different catalysts. They will be described in more detail later.

A component to be measured (CO) passes through a diffusion barrier 5, in this case a measuring orifice, to reach the measuring electrode 2 where it is oxidized to $CO_2$. At the same time, the oxygen in an air chamber 6 is reduced to water at the counter electrode. The dimensions of the air chamber are such that the atmospheric oxygen used up at the electrode causes only a slight change in the oxygen partial pressure of the air. Since the currents produced are in the range of nano amperes, they are amplified by means of a current amplifying circuit. For this purpose, the measuring electrode and counter electrode are connected to a suitable measuring amplifier 7 and resistor 8, the output of which is measured by meter 9.

The following examples for the measurement of CO, $H_2$ and hydrazine are given to enable a clear understanding of the sensors produced according to the invention. These cells are, of course, also suitable for the detection of those reducing substances which occur as cross sensitivities in the following examples. The examples describe the manufacture of the individual electrodes for the electro-chemical oxidation of CO, $H_2$ and hydrazine and the corresponding counter electrodes. They also describe the preparation of the electrolytes according to the invention. The examples show that using the cell according to the invention results in a gas measuring cell which is of the highest sensitivity as well as being sturdy and requiring little servicing.

EXAMPLE 1

A mixture of 15 g of arylic acid amide, 12.5 g of urea, 7.5 g of acetamide, 2.5 g of propionic acid nitrile and 50 g of a 30% phosphoric acid is heated to 60° C. in a glass beaker, and solution polymerization is initiated by the addition of 2.5 ml of a saturated potassium peroxidisulphate solution. After the onset of polymerization, the mixture, which is now in the form of a thick liquid, is poured into a cylinder 2 cm in height and of 1.6 cm internal diameter. After termination of polymerization and cooling, the electrolyte sets to a solid, sticky gel.

2 discs 1.6 cm in diameter are punched out of a sheet of carbon fleece ca. 0.2 mm in thickness, and each disc is brought into contact with a thin platinum wire. These discs, which serve to conduct away the current, are placed on the two sides of the electrolyte surface, where they become firmly anchored by the good adhensive properties of the gel. Finely divided platinum black is then advantageously applied to the electrolyte with carbon fleece in much the same way as in a screen printing process by applying ca. 5 mg of platinum per $cm^2$ through a fine meshed plastics net.

The resulting measuring cell is provided with a diffusion barrier in the form of an orifice 5×0.3 mm in diameter on the side of the measuring electrode and is sealed off with a plastic cap on the side of the counter electrode (cathode). The volume of the air chamber above the cathode is ca. 1 cc. The measuring sensitivity for CO is of the order of 8 nA/ppm.

EXAMPLE 2

Measuring cells according to Example 1 were produced in which 50 g of Mg $(C10_4)_2$ were added as a hygroscopic substance in addition to the polymer composition described. The measuring cells manifested the same behavior as in Example 1 but only slight strinkage of the gel due to water loss was observed, even after 3 months.

EXAMPLE 3

In the manufacture of this cell, the gel forming substance was first separately prepared by solvent polymerization, i.e. a mixture of 15 g of acrylic acid amide, 12.5 g of urea, 7.5 g of acetamide and 2.5 ml of propionic acid nitrile in 200 ml of water was reacted at 60° by the addition of 2.5 ml of a saturated $K_2S_2O_8$ solution. The reaction product was precipitated with acetone, filtered and dried. The electrolyte solution consisting of 50 ml of 2 N sulphuric acid and 50 g of Mg $(C10_4)_2$ was added to 20 g of this reaction product, which was then poured into the cell body. When gel formation was completed, the electrolyte was covered on both surfaces with carbon fleece discs 0.2 mm in thickness which had previously been brought into contact with a thin platinum wire. 5 mg of platinum black per $cm^2$ was then applied to both carbon fleece as in Example 1. The resulting measuring cell was provided with a diffusion barrier and plastics cap as in Example 1. The sensitivity of measurement for CO was ca. 8 nA/ppm.

EXAMPLE 4

A measuring cell was produced, using carbon fleece to conduct away current and platinum black as catalyst. To ensure that the platinum black would be bonded to the fleece, the fleece was first soaked in a dilute polymer solution of 10 parts of water and 1 part of polyacrylamide and was then uniformly coated with platinum black (5 mg of platinum per $cm^2$). The electrodes treated as described above, were dried in air and then glued to both sides of the gel electrolyte. The aqueous gel electrolyte consisted of 2 N sulphuric acid and the reaction product of polyacrylamide, urea and acetamide and was prepared as in Example 1.

The resulting measuring cell, which had a diameter of 1.6 cm and a height of 2 cm, was provided with a diffusion barrier (restrictor orifice) as in Example 1 and sealed off with a plastic cap on the side of the cathode. The cell had a measurement sensitivity for carbon monoxide of 12 nA/ppm and a delay time $t_{90}$ of ca 2 minutes. The measurement sensitivity for hydrogen was found to be 20 nA/ppm and the delay time $t_{90}$ ca. 90 seconds.

EXAMPLE 5

For the production of this measuring cell, a gel electrolyte based on polyacrylamide and phosphoric acid was prepared. The gel electrolyte was obtained by the polymerization at 70° C. of acrylic acid amide (10% by weight) in a 60% by weight phosphoric acid solution with the addition of 1% by weight of $K_2S_2O_8$ solution. To produce the electrodes, carbon fleece was used to conduct away current and platinum black as a catalyst. To bond the platinum black to the fleece, the fleece was first soaked in a dilute polymer solution consisting of 20 parts of water and 1 part of polyacrylamide and then uniformly coated with platinum black (5 mg of $Pt/cm^2$). After repeated impregnation with the dilute gel electrolyte solution to fix the platinum black powder, the resulting electrode was dried in a desiccator. Two discs 1.6 cm in diameter were then punched out and each was brought into contact with a thin platinum wire. The resulting electrodes were placed on the electrolyte surfaces on both sides and firmly anchored to the gel by light application of pressure.

The sensitivity of measurement of the measuring cell for CO was 12 nA/ppm and its delay time $t_{90}$ ca. 2 minutes.

EXAMPLE 6

Traces of hydrazine gas were measured with a measuring sensor similar to those described in the above Examples. The electrolyte was prepared by the polymerization of 15 g of acrylic acid amide, 12.5 g of urea and 1.5 ml of formaldehyde solution (35% by weight) in a solution of 60 g of $Mg(ClO_4)_2$ in 50 ml of water. A carbon fleece to which a thin gold layer had been applied by vaporization under vacuum was used as working or measuring electrode.

The counter electrode was an atmospheric oxygen electrode with platinum as catalyst, the preparation of which is described in Example 1 to 6. The specific sensitivity for hydrazine was ca. 1,000 nA/ppm.

We claim:

1. In an electro-chemical sensor for the measurement of carbon monoxide, hydrogen or hydrazine in ambient air, comprising a catalyst containing measuring electrode exposed to ambient air and communicating through an aqueous acid electrolyte with a non-polarizable counter electrode, the improvement comprising:
    (a) a body of an aqueous hygroscopic polymer gel in which ionogenic substances are dissolved, the gel body having sticky surfaces,
    (b) the measuring electrode comprising a porous sheet-like matrix, coated with catalyst particles,
    (c) the matrix being firmly anchored at the surface of the polymer gel in a self-supporting manner and the catalyst particles being embedded with part of their surfaces in the gel and with the remaining surface portions protruding from the gel.

2. The sensor according to claim 1, wherein the matrix consists of a meshed electrically conductive grid, which is applied to the gel electrolyte by pressure.

3. The sensor according to claim 1 or 2, for the measurement of carbon monoxide and hydrogen, wherein the matrix and the counter electrode consists of a graphite fleece and the catalyst is platinum.

4. The sensor according to claim 1 or 2, for the measurement of hydrazine, wherein the matrix consists of a carbon fleece coated with gold and the counter electrode consists of a carbon fleece coated with platinum black.

* * * * *